United States Patent [19]

Hutson, Jr.

[11] 4,053,535

[45] Oct. 11, 1977

[54] PROCESS FOR PRODUCING ISOPARAFFIN-OLEFIN ALKYLATE HAVING IMPROVED OCTANE NUMBER

[75] Inventor: Thomas Hutson, Jr., Bartlesville, Okla.

[73] Assignee: Phillips Petroleum Company, Bartlesville, Okla.

[21] Appl. No.: 689,760

[22] Filed: May 25, 1976

[51] Int. Cl.² .............................................. C07C 3/54
[52] U.S. Cl. ............................................... 260/683.49
[58] Field of Search ...................... 260/683.48, 683.49, 260/683.43, 683.58

[56] References Cited

U.S. PATENT DOCUMENTS

| | | |
|---|---|---|
| 2,332,527 | 10/1943 | Pyzel ............................. 260/683.58 |
| 2,403,922 | 7/1946 | Hawthorne ..................... 260/683.58 |
| 2,502,333 | 3/1950 | Meadow et al. ................ 260/683.48 |
| 2,824,162 | 2/1958 | Knight et al. .................. 260/683.58 |
| 3,133,128 | 5/1964 | McDonald ...................... 260/683.48 |
| 3,281,213 | 10/1966 | Waddill .......................... 260/683.48 |
| 3,286,992 | 11/1966 | Armeniades et al. ............... 259/4 X |
| 3,346,660 | 10/1967 | Hutson, Jr. et al. ........... 260/683.49 |
| 3,478,125 | 11/1969 | Chapman ....................... 260/683.48 |
| 3,775,510 | 11/1973 | Hutson, Jr. et al. ........... 260/683.48 |

Primary Examiner—George Crasanakis

[57] ABSTRACT

An isoparaffin - olefin alkylate of improved octane number is produced by passing total hydrocarbon reactants through a static mixing zone prior to passing the reactants to a riser-reactor admixed with HF acid catalyst. The total hydrocarbon reactants include HF-free isoparaffin recycled stream.

2 Claims, 1 Drawing Figure

U.S. Patent
Oct. 11, 1977
4,053,535
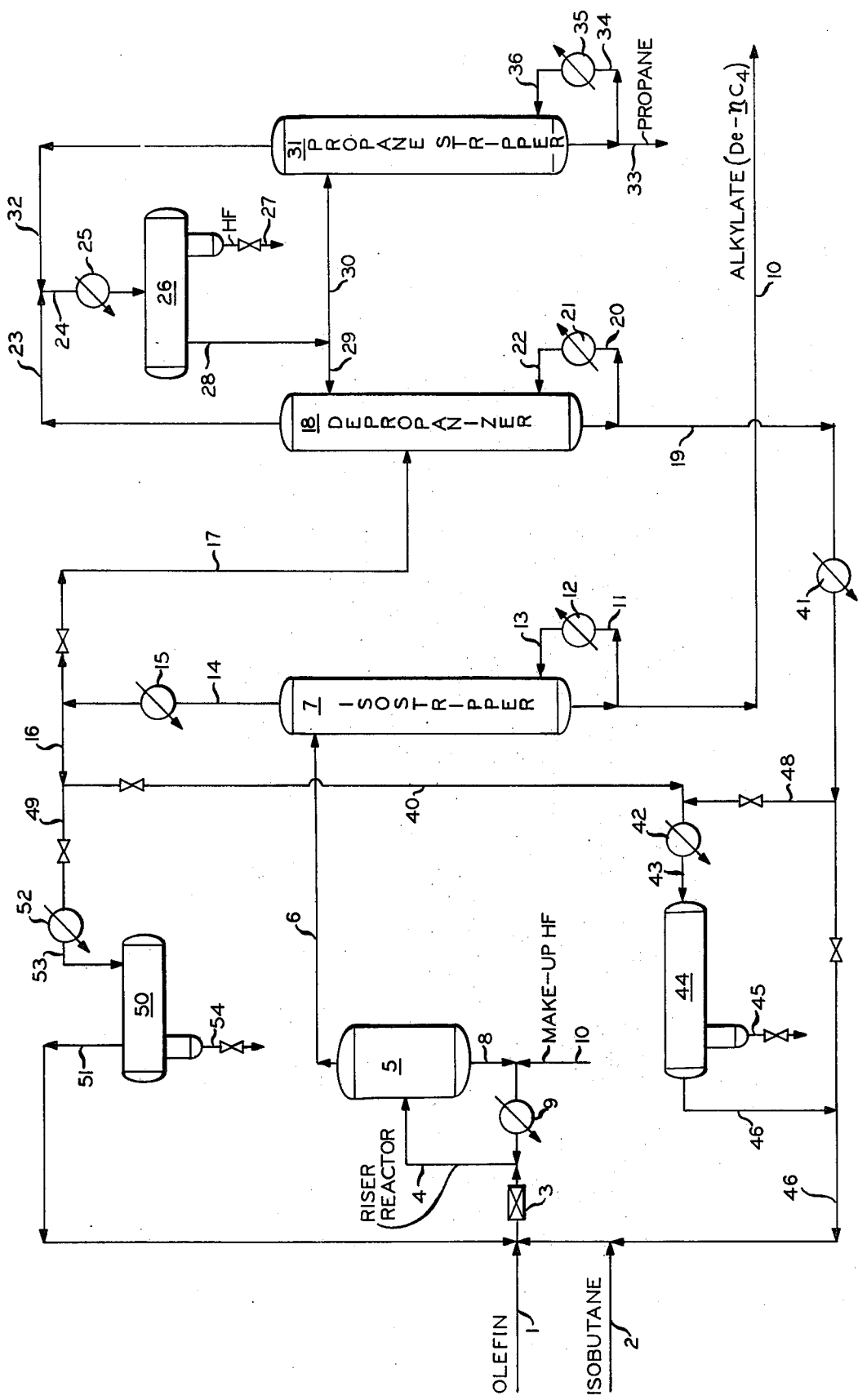

PROCESS FOR PRODUCING ISOPARAFFIN-OLEFIN ALKYLATE HAVING IMPROVED OCTANE NUMBER

BACKGROUND OF THE INVENTION

This invention relates to an improved process of alkylation of at least one isoparaffin with at least one olefin in the presence of an acid catalyst. In particular, it relates to production of a higher octane alkylate as the result of a thorough admixing of feed and/or recycled isoparaffin with the feed olefin prior to adding acid catalyst.

In the process of alkylation of an isoparaffin with an olefin in the presence of an acid catalyst, both reactants are introduced into pipes leading to the reactor. A portion of the isoparaffin introduced can be a recycled isoparaffin recovered in the later part of the process. Prior to the introduction of the catalyst, the reactants are subjected only to pipe or pipe and pump mixing. The present invention deals with an improved method for treating reactants prior to their introduction into the alkylation reactor.

One object of the present invention is to provide an improved method for the operation of an alkylation system.

Another object of this invention is to improve octane values of alkylate produced by alkylation of an isoparaffin with an olefin in the presence of an acid catalyst.

Other objects of the invention will become apparent to those skilled in the art upon studying this specification and appended claims.

BRIEF DESCRIPTION OF THE DRAWING

The drawing represents a schematic diagram of the process of alkylation of an isoparaffin with an olefin in the presence of an acid catalyst to which the present invention is applicable.

SUMMARY OF THE INVENTION

In accordance with one aspect of the invention in the process of alkylation of at least one isoparaffin with at least one olefin both are thoroughly admixed prior to introduction of at least a preponderance of the catalyst resulting in an alkylate having an improved octane value.

Other aspects of the invention will become apparent to those skilled in the art upon studying this disclosure.

DETAILED DESCRIPTION OF THE INVENTION

This invention is applicable to a process of alkylation of at least one isoparaffin with at least one olefin in the presence of an acid catalyst. A mixer is provided for thorough mixing of the isoparaffin stream with the olefin stream before at least a preponderance of acid catalyst is added to the reactants. Surprisingly, it was discovered that such mixing results in an alkylate having a higher octane number than that of the alkylate produced by a process utilizing mere pipe mixing, or pipe and pump mixing.

In general, the isoparaffin to olefin mole ratio range is from about 2 to 1 up to about 25 to 1, usually from about 4 to 1 up to about 15 to 1. The total hydrocarbon to HF catalyst volume ratio range is from about 1/10 to about 10/1.

The HF alkylation reaction is usually carried out in a temperature range of about 0° F (-18° C) to about 150° F (66° C) and at a pressure sufficient to maintain liquid phase conditions. Lowering of the reaction temperature results in an alkylate of higher octane number.

Any isoparaffin, alone or in admixture with another isoparaffin, is suitable for the use with the present invention including: isobutane, isopentane, and isohexanes. Among olefins that can be used are: propylene, butylenes, amylenes and many others either alone or in admixture with other olefins. Some of the reactants may be recycled reactants containing small amounts of impurities such as HF; however, substantially all of the HF catalyst is added in accordance with this invention after thorough mixing of the reactants.

Referring now to the drawing, olefin feed passed by 1 comes together with isobutane recycle feed passed by 51 and 46 and isobutane makeup feed passed by 2. The mixture enters a static mixer 3 where it is thoroughly mixed and goes from there into a riser-reactor 4 where alkylation with hydrofluoric acid catalyst under alkylation conditions is effected. Instead of a single riser-reactor 4, the process can include an agitated reaction zone, or section, and a separate settler zone, section, or vessel. From reaction riser-reactor 4 reaction mass is passed to the phase separator 5. There alkylation reactor effluent forms an upper hydrocarbon phase, which is passed by 6 to isostripper 7. The lower phase containing hydrofluoric acid catalyst is passed from the phase separator 5 by 8 to a cooler 9 back to riser-reactor 4. Make-up HF catalyst can be supplied to 8 through 10. A bottoms taken from the isostripper 7 by 10 after removal of normal butane and after usual chemical or other treatment, is suitable for use as blending stock in the production of motor fuels. For column reboil purposes, the bottom of column 7 is heated by recycling a portion of bottoms product by 11, heater 12, and 13 from 10 to the tower bottom. The overhead from column 7 passes by 14 through cooler 15, and splits into stream 16 and stream 17. The latter is passed to depropanizer 18 which removes propane as overhead 23, thus preventing propane buildup in the system. The isobutane passing as bottoms through 19 is cooled in 41. A portion of bottoms going through 19 is recycled by 20, through the heater 21, and 22 to the depropanizer 18 to reboil the bottoms. The depropanizer overhead passed by 23 and 24 into cooler 25 goes into accumulator 26, from which a liquid HF phase is withdrawn at 27 and can be recycled to the alkylation step or otherwise used. One portion of a hydrocarbon phase taken from accumlator 26 by 28 is passed by 29 as reflux to the top of depropanizer 18. The second portion of a hydrocarbon phase taken from accumulator 26 by 28 is passed by 30 into propane stripper 31. An overhead containing HF and some propane is passed from propane stripper 31 by 32 and 24, and cooler 25 to accumulator 26. The bottoms from the propane stripper 31 are removed at 33. A portion of the stream 33, is passed by 34 through heater 35, and 36 back to propane stripper 31 bottom, the other portion is taken out of the system as propane yield.

Returning now to stream 16 to stream 19, a portion of stream 16 is passed by 40 through cooler 42. Entire stream 19 is chilled by cooler 41 and portion of the stream can be further chilled by going through 48 into cooler 42. The streams chilled in 42 are passed by 43 to a phase separator 44. The lower phase containing mainly HF is removed by 45. The upper phase containing mainly isobutane is passed by 46, to the static mixer 3.

The other portion of stream 16 passes through 49, a cooler 52, and 53 into accumulator 50. The lower phase containing mainly HF is removed from the accumulator 50 through 54 whereas the upper phase, containing mainly isobutane, is passed by 51 to the static mixer 3.

Coolers 9, 15, 25, and 41 are conventional indirect heat exchangers employing water as the coolant; the product leaves these exchangers at about 100° F (38° C), in the conventional operation.

Exchangers 42 and 52 are conventional refrigerated indirect heat exchangers, which use a refrigerant, such as propane, to attain temperatures lower than those attained by conventional cooling water. Streams 16 and 19 can be separately refrigerated in refrigerated coolers 42 and 52, or the two streams may be combined and chilled in either cooler 42 or 52.

Although the invention has been described here in terms of a specific process, this process is chosen for illustrative purposes only and is not intended to limit the scope of the invention as set forth in the claims. For example, although HF removal by chilling is shown in the process, the invention is applicable to a process in which HF is removed by any other suitable method such as by neutralization, by water wash and drying, or by contacting with clays, etc.

Furthermore, although a static mixer operating on the general principle disclosed for example in U.S. Pat. No. 3,286,992 is utilized in connection with the present invention, the use of this type of a mixer is merely preferred. Any other suitable mixer such as jet mixers, orfice mixers, rotating impeller mixer described for example in *Perry's Chemical Engineering Handbook*, 4th edition, may be employed instead.

The following example merely illustrates the invention.

EXAMPLE

Isobutane and olefin were introduced into a pilot plant alkylation system similar to the one illustrated in the figure. The catalyst employed was hydrofluoric acid. The recycled isobutane was chilled to about 40° F (4° C) in a cooler and the hydrofluoric acid was separated from the recycled isobutane in a phase separator. In the first run, mixer 3 was not used. The isobutane and olefin were merely combined in a pipe before being introduced into the reactor. In the second run, Kenics mixer ws used to thoroughly admix isobutane and olefin. The ingredients were heated in Kenics mixer to attain comparable reactor entry temperature for Run 2 as for Run 1. The heating proceeded further than desired so that the temperature in Run 2 was higher than that in Run 1. The octane number of the alkylate produced in each run was measured by ASTM-908-64. Following results were obtained:

|  | Run 1 | Run 2 |
|---|---|---|
| Isobutane/Olefin Volume Ratio | 12:1 | 12:1 |
| Catalyst/Hydrocarbon Volume Ratio | 3:1 | 3:1 |
| Reactor Inlet Temperature, ° F., | 60 | 70 |
| Alkylate, RON clear, | 93.0 | 94.5 |

The results indicate that higher octane alkylate can be obtained by thoroughly mixing the isobutane and olefin prior to adding HF catalyst. It should be emphasized that even higher increase of octane number would occur if the temperature of Run 2 was equal to that of Run 1.

I claim:
1. A process for producing alkylate having an improved octane number which comprises:
    a. passing total hydrocarbon reactants comprising isoparaffin and olefin through a static mixing zone and therein subjecting said isoparaffin and olefin to thorough mixing;
    b. introducing the mixture of isoparaffin and olefin after passing through said static mixing zone to a riser-reactor in admixture with HF acid catalyst at liquid phase and reaction conditions to convert at least a substantial portion of isoparaffin and olefin into alkylate;
    c. passing the reaction effluent of step (b) to a first settling zone and allowing the reaction effluent to separate into an upper phase comprising hydrocarbons and a lower phase comprising HF;
    d. passing said upper phase to a fractionation zone and therein subjecting same to distillation conditions to separate said upper phase into a fraction comprising alkylate and a fraction comprising isoparaffin;
    e. withdrawing the isoparaffin fraction from step (d) and refrigerating same to a sufficiently low temperature to allow separation of traces of HF still remaining in the isoparaffin fraction;
    f. passing the refrigerated isoparaffin stream to a second settling zone and allowing same to separate therein into an upper isoparaffin phase and a lower HF phase;
    g. recycling a substantially HF-free isoparaffin stream separated in (f) to said mixing zone; and
    h. withdrawing the alkylate separated in step (d) as product, said alkylate having a higher octane value than alkylate produced by the same process, but without step (a).
2. A process according to claim 1 wherein said isoparaffin is isobutane and said olefin is at least one of propylene, butylene, and amylene.

* * * * *